United States Patent [19]

Hök

[11] 4,297,890
[45] Nov. 3, 1981

[54] PRESSURE TRANSDUCER

[75] Inventor: Bertil Hök, Uppsala, Sweden

[73] Assignee: Siemens Aktiengesellschaft, Berlin & Munich, Fed. Rep. of Germany

[21] Appl. No.: 151,771

[22] Filed: May 21, 1980

[30] Foreign Application Priority Data

Jun. 7, 1979 [DE] Fed. Rep. of Germany ....... 2923122

[51] Int. Cl.³ .............................................. G01L 9/02
[52] U.S. Cl. ..................................... 73/753; 128/673; 128/675; 338/38
[58] Field of Search .................. 73/753, 733; 128/673, 128/674, 675, 723; 338/36, 38, 86

[56] References Cited

U.S. PATENT DOCUMENTS

| | | | |
|---|---|---|---|
| 2,769,070 | 9/1979 | Donald | 338/38 |
| 3,911,902 | 10/1975 | Delphy | 128/675 |
| 3,942,382 | 3/1976 | Hok | 73/753 |
| 4,261,208 | 4/1981 | Hok et al. | 73/753 |

Primary Examiner—Donald O. Woodiel

Attorney, Agent, or Firm—Hill, Van Santen, Steadman, Chiara & Simpson

[57] ABSTRACT

In an exemplary embodiment, a measuring cell is formed by an interior tube open at one end and within a surrounding exterior tube. The interior tube is adapted to contain a gas while a chamber within the exterior tube at the open end of the interior tube can be filled with a pressure transmission liquid via a channel extending within the exterior tube and along the length of the interior tube and leading to the chamber. For a pressure measurement, the liquid in the chamber can communicate directly with a liquid in a liquid vessel, e.g. a blood vessel. In the measuring cell electrodes are arranged for generating an electric signal which corresponds to the gas volume in the measuring cell and thus the liquid pressure in the chamber. The measuring cell is disposed with its open end opposite a lateral opening in the wall of the exterior tube. The lateral opening communicates with the chamber at a location transversely offset relative to the open end of the measurement cell and disposed so as to facilitate and safeguard preparation of the device for a pressure measurement.

5 Claims, 2 Drawing Figures

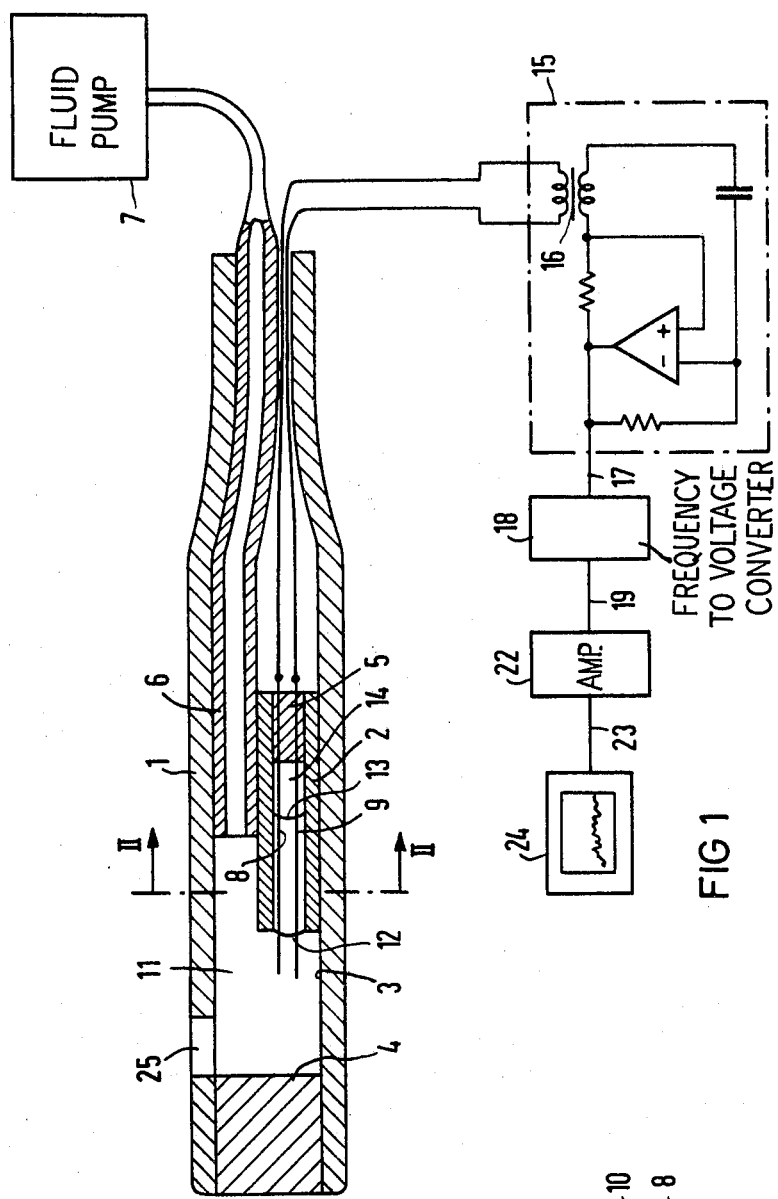
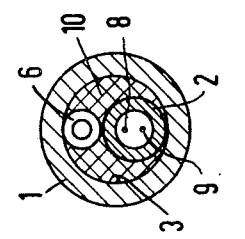

PRESSURE TRANSDUCER

CROSS REFERENCE TO RELATED APPLICATION

The present application is an improvement over Hoek et al pending application U.S. Ser. No. 011,864 filed Feb. 13, 1979, now U.S. Pat. No. 4,261,208, and the detailed description and drawings of this pending application are incorporated herein by reference, by way of background.

BACKGROUND OF THE INVENTION

The invention relates to a pressure transducer for generating an electric signal which corresponds to a liquid pressure to be measured in a liquid vessel, said transducer comprising a measuring cell, arranged in an exterior tube, which measuring cell can be filled partially with a pressure transmission liquid and for the remainder with a gas, wherein leading away from the measuring cell there is a liquid pressure transmitting chamber at the measurement end of the exterior tube capable of being filled with the pressure transmission liquid which chamber can be directly connected in pressure transmitting relation with the liquid in the liquid vessel; in the measuring cell, means are arranged for generating an electric signal which corresponds to the gas volume in the measuring cell, the measuring cell comprising an interior tube, surrounded by the exterior tube, whereby, between the exterior and interior tube, a channel is left open for the passage of the pressure transmission liquid during filling of the chamber, the interior tube being closed at its end remote from the measuring end of the pressure transducer.

A pressure transducer of this type, which is a miniature pressure transducer, is known from the German OS No. 2,811,859 which corresponds to the above identified copending application. This pressure transducer exhibits a measuring end with an axial opening which is disposed longitudinally opposite the opening of the measuring cell. However, the pressure transducer, before it is conveyed into a liquid vessel, must itself be filled with a pressure transmission liquid. In so doing, it is easy for the pressure transducer filled with the pressure transmission liquid to incur impact. In the case of impact of the pressure transducer, however, pressure transmission liquid then drops out of the frontal axial opening at the measurement end on account of the special frontal position of the opening. As a consequence, air which is in the measuring cell is drawn out of the open end of the measuring cell. This leads to erroneous measured values. In addition, in the case of a pressure transducer introduced in a liquid vessel, the opening at the measurement end of the exterior tube can readily become clogged. Further, in the case of the pressure transducer of the aforesaid copending application, additional arrangements and special methods must be employed in order to fill the measuring cell partially with the transmission liquid, so that the position of the meniscus between the transmission liquid and air in the measuring cell can be established. This is very difficult and cumbersome.

An additional pressure transducer, which is also a miniature pressure transducer, is known from the German OS No. 2,447,529 and U.S. Pat. No. 3,942,382. In the case of this pressure transducer, a thin capillary tube projects axially into the measuring cell and connects an interior tube, which serves the purpose of supply of the transmission fluid, with the chamber at the measurement end which is capable of being filled with this liquid, which chamber can be directly connected with the liquid vessel; i.e., a blood vessel, via a suitable connector. When the pressure transducer and connector are being filled with transmission fluid, for example a physiological saline solution, this liquid flows via the interior tube through the capillary and into the chamber which is capable of direct communication via the connector with the liquid vessel on account of an axial opening of the pressure transducer at its measurement end. Due to the position of the opening of the pressure transducer, the latter pressure transducer is subject to the same disadvantages as the pressure transducer of the German OS No. 2,811,859. During filling of the pressure transducer with the transmission fluid, a meniscus between this liquid and the gas volume at the end of the capillary tube between the interior wall of the exterior tube and the exterior wall of the capillary tube is to be formed. This meniscus must have a specified position in the measuring cell in order that satisfactory measuring results can be obtained. If the capillary tube, which is to project axially into the measuring cell disposed in the exterior tube, is somewhat bent, or does not lie precisely axially, this can lead to non-linear readings. Furthermore, the pressure transducer is complicated in its structure due to the capillaries.

SUMMARY OF THE INVENTION

The object underlying the invention resides in further developing a pressure transducer of the type initially cited such that it is very simple in construction but nonetheless still safeguarded against malfunctions, so that satisfactory measurements can always be carried out.

This object is solved in accordance with the invention in that the measuring cell, with its open end, is disposed opposite a lateral opening in the wall of the exterior tube which lateral opening can also provide the communication with the liquid vessel whose liquid pressure is to be measured.

On account of the lateral position of the opening in the tube wall, the pressure transmission liquid in the pressure transducer always remains in place even in the case of more violent impacts of the pressure transducer. In addition, with the lateral position of the opening, the danger does not exist that the opening will become clogged. In the case of a measurement of the liquid pressure in a vessel of a patient, not the kinematic pressure (i.e. pressure due to the flow of liquid) but the hydrostatic pressure—i.e., the pressure of the liquid itself, is measured.

In an advantageous further development of the invention it is proposed that two longitudinally extending electrodes arranged in laterally spaced relation in the interior tube be extended to project from the open end of the interior tube. The electrodes may be connected to a circuit arrangement for measurement of the resistance between them. It is thereby achieved that, in the case of a filling of the pressure transducer with pressure transmission liquid, a meniscus is formed precisely at the free end of the measuring cell. This signifies that no additional devices for filling the pressure transducer need be present and that no special methods need be employed in order to establish a precise position of the meniscus.

The invention shall be explained in greater detail in the following on the basis of an exemplary embodiment serving the purpose of blood pressure measurement, illustrated in the drawings; and other objects, features and advantages will be apparent from this detailed disclosure and from the appended claims.

BRIEF DESCRIPTION OF THE DRAWINGS

FIG. 1 shows a longitudinal section of an inventive pressure transducer; and

FIG. 2 shows a diagrammatic indication of a cross section of the pressure converter of FIG. 1 taken generally according to the line II—II.

DETAILED DESCRIPTION

FIG. 1 shows that the pressure transducer, which is a miniature pressure transducer such as described in U.S. Pat. No. 3,942,382, exhibits an exterior tube 1 as well as an interior tube 2, surrounded by the exterior tube, which interior tube forms a measuring cell. The exterior tube is closed at its free or measurement end by means of a plug 4. The measuring cell 2 is eccentrically arranged in the exterior tube 1 and secured to its interior wall 3. The measuring cell 2 is closed at its end 5 remote from the plug 4 of the exterior tube 1, and thus remote from the measurement end of the pressure transducer. The measuring cell 2, moreover, terminates at a spatial interval from the plug 4 of the exterior tube. The measuring cell is disposed, with its open end, transversely opposite a lateral opening 25 in the exterior tube 1 of the pressure transducer. Between the exterior tube 1 and the measuring cell 2, a space has been left for accommodating a liquid line or channel 6 which is connected to a liquid pump 7 with sodium chloride solution. The liquid pump 7 can be a receptacle in which the sodium chloride solution is under a specific pressure. The liquid flow resistance; i.e., the diameter, of the liquid line 6 is matched to the desired liquid flow. In the measuring cell 2, two electrodes 8, 9, consisting of platinum, are arranged at an interval from each other and both extending in the direction of the tube length. The electrodes 8, 9 project from the free end of the measuring cell 2 by a substantial distance in comparison to their separation and are connected to a circuit arrangement, to be described in greater detail later, for the purpose of measurement of the resistance between them.

In FIG. 2, it is shown that the measuring cell 2 and the liquid line 6 are embedded in silicon rubber 10 so that the end of the exterior tube remote from the measurement end is completely sealed off.

If a blood pressure measurement is to be conducted, the pressure transducer must be filled with sodium chloride solution before it is applied directly at the measuring area—for example in a blood vessel. Sodium chloride solution flows from the liquid pump 7 via the liquid line 6 into the chamber 11 and presses the air contained in the pressure transducer out into the atmosphere via the opening 25. Due to the small dimensions of the pressure transducer, the sodium chloride solution, dependent upon the pressure of the liquid pump 7, does not flow out into the atmosphere, but fills the chamber 11 within the exterior tube 1. Due to the design and position of the measuring cell 2, the air disposed therein is not removed. Approximately 0.01 mm from the free end of the measuring cell a meniscus 12 is formed in the measuring cell 2.

The pressure transducer is now conveyed into a blood vessel of a patient for a blood pressure measurement, whereby the gas volume 14 enclosed in the measuring cell 2 changes. Due to the fact that the electrodes 8, 9, project from the measuring cell 2, the position of the meniscus 12 need not be changed. The respective gas volume for example as represented by meniscus position 13 corresponds to the pressure of the sodium chloride solution and hence to the pressure to be measured, and is converted into an electric signal via the electrodes 8, 9.

The resistance between the electrodes 8, 9 is dependent upon the position of the meniscus which restricts the air volume 14. This resistance influences (or affects) the frequency of an oscillator 15. In the case of connection of the pressure transducer, or of the electrodes 8, 9, with the secondary winding of a transformer 16 of the oscillator 15, a complete galvanic insulation between the pressure transducer and the oscillator 15 is obtained, which is desirable for safety reasons. An oscillator of this type is described e.g. in the reference "Operational Amplifiers", page 370, McGraw-Hill, New York, 1971. The oscillator 15 is connected, via the connection 17, with an apparatus 18 for converting the frequency into a corresponding voltage. The apparatus 18, in turn, is connected, via the connection 19, with an amplifier 22 for the purpose of amplifying the signals from apparatus 18. The amplifier 22, in turn, is connected, via the connection 23, with a recording apparatus 24 for recording the measurement results.

The dimensions of the pressure converter can be kept very small. In the case of one exemplary embodiment, the exterior diameter of tube 1 was 0.9 mm and the length 4 mm. Due to the fact that the opening 25 of the pressure transducer is laterally arranged in the exterior tube 1, a satisfactory pressure measurement can be conducted via such opening without the danger existing that the opening will become clogged during measurement.

It will be apparent that many modifications and variations may be effected without departing from the scope of the novel concepts and teachings of the present invention.

SUPPLEMENTAL DISCUSSION

By way of example, the pressure transducer of the present invention may be mounted in an open longitudinal groove or channel of a catheter-carrier such as shown in the second and third figures of an article entitled "A New Multi-Transducer Catheter for Intraluminal Pressure Recording in Vivo" by Ulmsten, Froman, Hoek, et al, *Electromedia* 1/80, pages 9–12. When so mounted, the lateral opening 25 of the transducer is in radial registration with the open side of the groove or channel of the carrier so as to be in direct fluid communication with the liquid of the vessel or organ in which the carrier has been inserted (without the interposition of any flexible pressure transmitting membrane or the like).

I claim as my invention:

1. A pressure transducer for generating an electrical signal which corresponds to a liquid pressure to be measured within a liquid vessel, said transducer comprising:

an exterior tube (1) having a measurement chamber (11) at a measurement end thereof for direct communication with a liquid pressure to be measured, an interior tube (2) disposed longitudinally within said exterior tube and having a closed end (5) remote from said chamber and having an open end opening at said chamber for direct fluid communication with a liquid in said chamber, liquid supply means (6) within said exterior tube and communicating with said chamber, said liquid supply means providing for the filling of said chamber with a pressure transmission liquid while a gas is entrapped within said interior tube, said interior tube (2) providing a pressure measuring cell and having sensing means for supplying an electric signal which is a function of the gas volume within said interior tube and thus of the liquid pressure in said chamber, said exterior tube (1) having an exterior wall with a lateral opening (25) communicating with said chamber transversely opposite from the open end of said interior tube, and means comprising said lateral opening (25) for placing said chamber (11) and the open end of said interior tube (2) in direct fluid communication with the liquid whose pressure is to be measured.

2. A pressure transducer according to claim 2, with said sensing means of said measuring cell comprising two elongated electrodes (8, 9) extending longitudinally within said interior tube in laterally spaced relation and projecting through the open end of said interior tube and into said chamber.

3. A pressure transducer according to claim 2, with circuit means connected with said electrodes for the measurement of the resistance therebetween and thereby to sense the volume of gas within said interior tube, as a measure of the pressure of a liquid coupled with the liquid in said chamber via said lateral opening (25).

4. A pressure transducer according to claim 1, with the size of said lateral opening (25) being such in relation to the pressure of pressure transmission liquid in said chamber that the pressure transmission liquid is held against leakage from said lateral opening (25) during handling of the exterior tube in the ambient atmosphere.

5. A pressure transducer according to claim 4, with said measurement end (4) being of a diameter to be axially inserted into a blood vessel while said lateral opening (25) provides a direct fluid coupling of the blood with said pressure transmission liquid.

* * * * *